(12) United States Patent
Smith et al.

(10) Patent No.: US 8,052,629 B2
(45) Date of Patent: Nov. 8, 2011

(54) MULTI-FIT ORTHOTIC AND MOBILITY ASSISTANCE APPARATUS

(75) Inventors: Jonathan Smith, Waterside (CA); Kern Bhugra, San Jose, CA (US)

(73) Assignee: Tibion Corporation, Sunnyvale, CA (US)

( * ) Notice: Subject to any disclaimer, the term of this patent is extended or adjusted under 35 U.S.C. 154(b) by 317 days.

(21) Appl. No.: 12/366,998

(22) Filed: Feb. 6, 2009

(65) Prior Publication Data
US 2009/0204038 A1 Aug. 13, 2009

Related U.S. Application Data

(60) Provisional application No. 61/027,365, filed on Feb. 8, 2008.

(51) Int. Cl.
*A61F 5/00* (2006.01)
*A61H 1/00* (2006.01)
*A61F 13/06* (2006.01)

(52) U.S. Cl. .................. 602/16; 602/5; 601/5; 128/882

(58) Field of Classification Search ............... 601/5, 33; 602/5, 23, 24, 25, 26, 27, 28, 29; 128/888, 128/882, 892; 623/24, 39, 47, 49
See application file for complete search history.

(56) References Cited

U.S. PATENT DOCUMENTS

| | | |
|---|---|---|
| 1,286,482 A | 12/1918 | Yoder |
| 1,366,904 A | 2/1921 | Davis |
| 1,391,290 A | 9/1921 | Welffens |
| 1,513,473 A | 10/1924 | Ackerman |
| 1,739,053 A | 12/1929 | Wilhelm |
| 1,847,720 A | 3/1932 | Marcellis |
| 2,169,813 A | 8/1939 | Parkin |
| 3,059,490 A | 10/1962 | McDuffie |
| 3,200,666 A | 8/1965 | Schrodt et al. |
| 3,358,678 A | 12/1967 | Kultsar |
| 3,398,248 A | 8/1968 | Klauss et al. |
| 3,402,942 A | 9/1968 | Shimano et al. |
| 3,631,542 A | 1/1972 | Potter |

(Continued)

FOREIGN PATENT DOCUMENTS

EP 1138286 A2 10/2001

(Continued)

OTHER PUBLICATIONS

International Search Report PCT/US2009/000811 dated Sep. 28, 2009; pp. 1-4.

(Continued)

*Primary Examiner* — Patricia Bianco
*Assistant Examiner* — Ophelia Hawthorne
(74) *Attorney, Agent, or Firm* — Shay Glenn LLP

(57) ABSTRACT

A multi-fit orthotic structure including an attachment system for coupling the orthotic structure to a wide variety of subjects without requiring a custom fit. In one embodiment, active mobility assistance is provided via an orthotic system capable of integrating a linear actuator and linkage system to deliver torque to the lower leg of a subject to facilitate flexion and/or extension motion of the subject's leg. The orthotic structure is attached to the subject using a textile suspension system which does not require the orthotic structure to interface directly in the knee region or at the lateral areas of the thigh and calf of the subject, thus providing an ideal fit for the widest possible range of subjects with the minimum number of required sizes.

3 Claims, 6 Drawing Sheets

U.S. PATENT DOCUMENTS

| | | | |
|---|---|---|---|
| 3,641,843 A | 2/1972 | Lemmens | |
| 3,863,512 A | 2/1975 | Crawley | |
| 3,899,383 A | 8/1975 | Schultz et al. | |
| 3,925,131 A | 12/1975 | Krause | |
| 3,976,057 A * | 8/1976 | Barclay | 601/34 |
| 4,507,104 A | 3/1985 | Clark et al. | |
| 4,549,555 A | 10/1985 | Fraser et al. | |
| 4,588,040 A | 5/1986 | Albright, Jr. et al. | |
| 4,649,488 A | 3/1987 | Osanai et al. | |
| 4,678,354 A | 7/1987 | Olsen | |
| 4,691,694 A | 9/1987 | Boyd et al. | |
| 4,697,808 A | 10/1987 | Larson et al. | |
| 4,731,044 A | 3/1988 | Mott | |
| 4,745,930 A | 5/1988 | Confer | |
| 4,754,185 A | 6/1988 | Gabriel et al. | |
| 4,796,631 A | 1/1989 | Grigoryev | |
| 4,807,874 A | 2/1989 | Little | |
| 4,872,665 A | 10/1989 | Chareire | |
| 4,878,663 A | 11/1989 | Luquette | |
| 4,883,445 A | 11/1989 | Gomoll et al. | |
| 4,922,925 A | 5/1990 | Crandall et al. | |
| 4,934,694 A | 6/1990 | McIntosh | |
| 4,944,713 A | 7/1990 | Salerno | |
| 4,953,543 A | 9/1990 | Grim et al. | |
| 4,981,116 A | 1/1991 | Trinquard | |
| 4,983,146 A | 1/1991 | Charles et al. | |
| 5,020,790 A | 6/1991 | Beard et al. | |
| 5,052,681 A | 10/1991 | Williams | |
| 5,078,152 A | 1/1992 | Bond et al. | |
| 5,117,814 A | 6/1992 | Luttrell et al. | |
| 5,170,777 A | 12/1992 | Reddy et al. | |
| 5,195,617 A | 3/1993 | Clemens | |
| 5,203,321 A | 4/1993 | Donovan et al. | |
| 5,209,223 A | 5/1993 | McGorry et al. | |
| 5,213,094 A | 5/1993 | Bonutti | |
| 5,239,222 A | 8/1993 | Higuchi et al. | |
| 5,241,952 A | 9/1993 | Ortiz | |
| 5,282,460 A | 2/1994 | Boldt | |
| 5,303,716 A | 4/1994 | Mason et al. | |
| 5,313,968 A | 5/1994 | Logan et al. | |
| 5,345,834 A | 9/1994 | Hayashi | |
| 5,358,468 A | 10/1994 | Longo et al. | |
| 5,378,954 A | 1/1995 | Higuchi et al. | |
| 5,421,798 A | 6/1995 | Bond et al. | |
| 5,440,945 A | 8/1995 | Penn | |
| 5,448,124 A | 9/1995 | Higuchi et al. | |
| 5,463,526 A | 10/1995 | Mundt | |
| 5,476,441 A | 12/1995 | Durfee et al. | |
| 5,509,894 A | 4/1996 | Mason et al. | |
| 5,520,627 A | 5/1996 | Malewicz | |
| 5,525,642 A | 6/1996 | Cipriano et al. | |
| 5,534,740 A | 7/1996 | Higuchi et al. | |
| 5,541,465 A | 7/1996 | Higuchi et al. | |
| 5,582,579 A | 12/1996 | Chism et al. | |
| 5,585,683 A | 12/1996 | Higuchi et al. | |
| 5,624,390 A | 4/1997 | Van Dyne | |
| 5,653,680 A | 8/1997 | Cruz | |
| 5,662,594 A | 9/1997 | Rosenblatt | |
| 5,662,693 A | 9/1997 | Johnson et al. | |
| 5,674,262 A | 10/1997 | Tumey | |
| 5,683,351 A | 11/1997 | Kaiser et al. | |
| 5,704,440 A | 1/1998 | Urban et al. | |
| 5,708,319 A | 1/1998 | Ban et al. | |
| 5,728,017 A | 3/1998 | Bellio et al. | |
| 5,746,684 A | 5/1998 | Jordan | |
| 5,746,704 A | 5/1998 | Schenck et al. | |
| 5,755,303 A | 5/1998 | Yamamoto et al. | |
| 5,789,843 A | 8/1998 | Higuchi et al. | |
| 5,833,257 A | 11/1998 | Kohlheb et al. | |
| 5,865,770 A | 2/1999 | Schectman | |
| 5,916,689 A | 6/1999 | Collins et al. | |
| 5,931,756 A | 8/1999 | Ohsono et al. | |
| 5,976,063 A | 11/1999 | Joutras et al. | |
| 6,001,075 A | 12/1999 | Clemens et al. | |
| 6,033,330 A | 3/2000 | Wong et al. | |
| 6,062,096 A | 5/2000 | Lester | |
| 6,119,539 A | 9/2000 | Papanicolaou | |
| 6,149,612 A | 11/2000 | Schnapp et al. | |
| 6,162,189 A | 12/2000 | Girone et al. | |
| 6,183,431 B1 | 2/2001 | Gach, Jr. | |
| 6,217,532 B1 | 4/2001 | Blanchard et al. | |
| 6,221,032 B1 | 4/2001 | Blanchard et al. | |
| 6,290,662 B1 | 9/2001 | Morris et al. | |
| 6,314,835 B1 | 11/2001 | Lascelles et al. | |
| 6,440,093 B1 | 8/2002 | McEwen et al. | |
| 6,472,795 B2 | 10/2002 | Hirose et al. | |
| 6,494,798 B1 | 12/2002 | Onogi | |
| 6,500,138 B1 | 12/2002 | Irby et al. | |
| 6,517,503 B1 | 2/2003 | Naft et al. | |
| 6,525,446 B1 | 2/2003 | Yasuda et al. | |
| 6,527,671 B2 | 3/2003 | Paalasmaa et al. | |
| 6,533,742 B1 | 3/2003 | Gach, Jr. | |
| 6,537,175 B1 | 3/2003 | Blood | |
| 6,554,773 B1 | 4/2003 | Nissila et al. | |
| 6,572,558 B2 | 6/2003 | Masakov et al. | |
| 6,599,255 B2 | 7/2003 | Zhang | |
| 6,659,910 B2 | 12/2003 | Gu et al. | |
| 6,666,796 B1 | 12/2003 | MacCready, Jr. | |
| 6,689,075 B2 | 2/2004 | West | |
| 6,694,833 B2 | 2/2004 | Hoehn et al. | |
| 6,709,411 B1 | 3/2004 | Olinger | |
| 6,796,926 B2 | 9/2004 | Reinkensmeyer et al. | |
| 6,805,677 B2 | 10/2004 | Simmons | |
| 6,821,262 B1 | 11/2004 | Muse et al. | |
| 6,827,579 B2 | 12/2004 | Burdea et al. | |
| 6,836,744 B1 | 12/2004 | Asphahani et al. | |
| 6,872,187 B1 | 3/2005 | Stark et al. | |
| 6,878,122 B2 | 4/2005 | Cordo | |
| 6,936,994 B1 | 8/2005 | Gimlan | |
| 6,966,882 B2 | 11/2005 | Horst | |
| 7,041,069 B2 | 5/2006 | West | |
| 7,124,321 B2 | 10/2006 | Garnett et al. | |
| 7,137,938 B2 | 11/2006 | Gottlieb | |
| 7,171,331 B2 | 1/2007 | Vock et al. | |
| 7,190,141 B1 | 3/2007 | Ashrafiuon et al. | |
| 7,192,401 B2 | 3/2007 | Saalasti et al. | |
| 7,239,065 B2 | 7/2007 | Horst | |
| 7,252,644 B2 | 8/2007 | Dewald et al. | |
| 7,324,841 B2 | 1/2008 | Reho et al. | |
| 7,365,463 B2 | 4/2008 | Horst et al. | |
| 7,396,337 B2 * | 7/2008 | McBean et al. | 601/5 |
| 7,410,471 B1 | 8/2008 | Campbell et al. | |
| 7,537,573 B2 | 5/2009 | Horst | |
| 7,559,909 B2 | 7/2009 | Katoh et al. | |
| 7,578,799 B2 * | 8/2009 | Thorsteinsson et al. | 602/5 |
| 7,648,436 B2 | 1/2010 | Horst et al. | |
| 7,731,670 B2 | 6/2010 | Aguirre-Ollinger et al. | |
| 7,880,345 B2 | 2/2011 | Hoffmann et al. | |
| 2001/0029343 A1 | 10/2001 | Seto et al. | |
| 2003/0104886 A1 | 6/2003 | Gajewski | |
| 2003/0120183 A1 | 6/2003 | Simmons | |
| 2003/0195638 A1 | 10/2003 | Kajitani et al. | |
| 2004/0015112 A1 | 1/2004 | Salutterback et al. | |
| 2004/0049139 A1 * | 3/2004 | Craciunescu | 602/13 |
| 2004/0054311 A1 | 3/2004 | Sterling | |
| 2004/0078091 A1 | 4/2004 | Elkins | |
| 2004/0106881 A1 | 6/2004 | McBean et al. | |
| 2005/0014600 A1 | 1/2005 | Clauson | |
| 2005/0085346 A1 | 4/2005 | Johnson | |
| 2005/0085353 A1 | 4/2005 | Johnson | |
| 2005/0101887 A1 | 5/2005 | Stark et al. | |
| 2005/0151420 A1 | 7/2005 | Crombez et al. | |
| 2005/0173994 A1 | 8/2005 | Pfister et al. | |
| 2005/0210557 A1 | 9/2005 | Falconer | |
| 2005/0221926 A1 | 10/2005 | Naude | |
| 2005/0245849 A1 | 11/2005 | Cordo | |
| 2005/0273022 A1 | 12/2005 | Diaz et al. | |
| 2006/0004265 A1 | 1/2006 | Pulkkinen et al. | |
| 2006/0069336 A1 | 3/2006 | Krebs et al. | |
| 2006/0132069 A1 | 6/2006 | Hemphill et al. | |
| 2006/0157010 A1 | 7/2006 | Moriwaki et al. | |
| 2006/0206045 A1 | 9/2006 | Townsend et al. | |
| 2006/0249315 A1 | 11/2006 | Herr et al. | |
| 2006/0251179 A1 | 11/2006 | Ghoshal | |
| 2006/0293624 A1 | 12/2006 | Enzerink et al. | |
| 2007/0015611 A1 | 1/2007 | Noble et al. | |
| 2007/0055163 A1 | 3/2007 | Asada et al. | |

| | | | |
|---|---|---|---|
| 2007/0155557 | A1 | 7/2007 | Horst et al. |
| 2007/0155558 | A1 | 7/2007 | Horst et al. |
| 2007/0155560 | A1 | 7/2007 | Horst et al. |
| 2007/0155588 | A1 | 7/2007 | Stark et al. |
| 2007/0162152 | A1 | 7/2007 | Herr et al. |
| 2007/0225620 | A1 | 9/2007 | Carignan et al. |
| 2007/0265534 | A1 | 11/2007 | Martikka et al. |
| 2007/0270265 | A1 | 11/2007 | Miller et al. |
| 2007/0287928 | A1 | 12/2007 | Kiviniemi et al. |
| 2008/0039731 | A1 | 2/2008 | McCombie et al. |
| 2008/0097269 | A1 | 4/2008 | Weinberg et al. |
| 2008/0195005 | A1 | 8/2008 | Horst et al. |
| 2008/0200994 | A1 | 8/2008 | Colgate et al. |
| 2008/0234608 | A1 | 9/2008 | Sankai |
| 2009/0007983 | A1 | 1/2009 | Healy |
| 2009/0036804 | A1 | 2/2009 | Horst |
| 2009/0048686 | A1 | 2/2009 | Ikeuchi et al. |
| 2009/0131839 | A1 | 5/2009 | Yasuhara |
| 2009/0171469 | A1 | 7/2009 | Thorsteinsson et al. |
| 2009/0260426 | A1 | 10/2009 | Lieberman et al. |
| 2009/0306548 | A1 | 12/2009 | Bhugra et al. |
| 2010/0038983 | A1 | 2/2010 | Bhugra et al. |
| 2010/0039052 | A1 | 2/2010 | Horst et al. |
| 2010/0049102 | A1 | 2/2010 | Yasuhara |
| 2010/0113986 | A1 | 5/2010 | Ashihara et al. |
| 2010/0114329 | A1 | 5/2010 | Casler et al. |
| 2010/0234775 | A1 | 9/2010 | Yasuhara et al. |
| 2010/0280628 | A1 | 11/2010 | Sankai |
| 2010/0318006 | A1 | 12/2010 | Horst |

FOREIGN PATENT DOCUMENTS

| | | | |
|---|---|---|---|
| JP | 63-136978 | A | 6/1988 |
| JP | 02-275162 | A | 11/1990 |
| JP | 04-104180 | A | 4/1992 |
| JP | 05-260766 | | 10/1993 |
| JP | 06-038551 | A | 2/1994 |
| JP | 07-274540 | A | 10/1995 |
| JP | 08-033360 | A | 2/1996 |
| JP | 08-149858 | | 6/1996 |
| JP | 08-154304 | A | 6/1996 |
| JP | 09-261975 | A | 10/1997 |
| WO | WO 90/11049 | A1 | 10/1990 |
| WO | WO 2005/057054 | A1 | 6/2005 |
| WO | WO 2007/027673 | A2 | 3/2007 |
| WO | WO-2007041303 | A2 | 4/2007 |

OTHER PUBLICATIONS

Advanced Mechatronics Lab (Univ. of Tokyo); Dual Excitation Multiphase Electrostatic Drive (DEMED); http://www.intellect.pe.u-tokyo.ac.jp/research/es_motor/demed_e.html; pp. 1-5; (printed) Nov. 21, 2002.
Advanced Mechatronics Lab (Univ. of Tokyo); High-power electrostatic motor; http://www.intellect.pe.u-tokyo.ac.jp/research/es_motor/es_motor_e.html; pp. 1-2; (printed) Nov. 21, 2002.
Advanced Mechatronics Lab (Univ. of Tokyo); Pulse driven induction electrostatic motor; http://www.intellect.pe.u-tokyo.ac.jp/research/es_motor/pim_e.html; pp. 1-5; (printed) Nov. 21, 2002.
ASEL (Univ. of Delaware); Powered orthosis project; http://www.asel.udel.edu/robotics/orthosis/orthosis.html, 1 pg. (update) Jan. 17, 1999.
British Tech. Group; Demonstration of energy saving in vehicles by integrating an infinitely variable transmission with an optimized petrol engine; prj. No. TR/00087/92; pp. 1-19; (version) Jul. 15, 1998.
Coronel et al; The Coronel effect positively infinitely variable transmission; U.C. Davis; No. 04CVT-51; pp. 1-8; 2004.
Fitch, C. J.; Development of the electrostatic clutch; IBM Journal; pp. 49-56; Jan. 1957.
Frank, Andrew; Engine optimization concepts for CVT-hybrid system to obtain the best performance and fuel efficiency; U.C. Davis; No. 04CVT-56; pp. 1-12; 2004.
Gongola et al.; Design of a PZT-actuated proportional drum brake; IEEE ASME Trans. on Mech.; vol. 4; No. 4; pp. 409-416; Dec. 1999.
Howard Leitch, PPT Ltd.; Waveform Gearing; Motion System Design; pp. 33-35; Nov. 2002.
James et al.; Increasing power density in a full toroidal variator; 3rd Int'l. IIR-Symposium; Innovative Automotive Transmission; pp. 1-11; Dec. 2004.
Kawamoto et al.; Power assist system HAL-3 for GAIT disorder person; ICCHP 2002; LNCS 2398; pp. 196-203; 2002.
Kim et al.; On the energy efficiency of CVT-based mobile robots; Proc. 2000 IEEE; Int. Conf. on Robotics & Automation; pp. 1539-1544; San Francisco, CA; Apr. 2000.
Kluger et al.; An overview of current automatic, manual and continuously variable transmission efficiencies and their projected future improvements; Int. Congress and Expo. (No. 1999-1-1259); pp. 1-6; Detroit, MI; Mar. 1-4, 1999.
Misuraca et al.; Lower limb human enhancer; Int. Mech. Eng. Conf. and Expo.; New York, NY; pp. 1-7; Nov. 11-16, 2001.
Niino et al.; Electrostatic artificial muscle: compact, high-power linear actuators with multiple-layer structures; Proc. IEEE Workshop on Micro Electro Mechanical Systems; Oiso, Japan; pp. 130-135; Jan. 1994.
Nugent, James; Design and performance of an exponential roller gear continuously variable transmission with band clutches; U.C. Davis; No. 04CVT-18; pp. 1-8; 2004.
Ohhashi, Toshio et al.; Human perspiration measurement; Physiological Measurement; vol. 19; pp. 449-461; 1998.
Otto Bock Health Care; (3C100 C-Leg® System) Creating a new standard for prosthetic control; http://www.ottobockus.com/products/op_lower_cleg.asp; pp. 1-2; (printed) Nov. 22, 2002.
Otto Bock Health Care; (3C100 C-Leg® System) New generation leg system revolutionizes lower limb prostheses; http://www.ottobockus.com/products/op_lower_cleg4.asp; pp. 1-2; (printed) Nov. 22, 2002.
Patras et al.; Electro-rheological fluids in the design of clutch systems for robotic applications; IEEE; pp. 554-558; Nov. 11-13, 1992.
Powell et al.; Computer model for a parallel hybrid electric vehicle (PHEV) with CVT; Proc. AACC; pp. 1011-1015; Chicago, IL; Jun. 2000.
Shastri et al.; Comparison of energy consumption and power losses of a conventionally controlled CVT with a servo-hydraulic controlled CVT and with a belt and chain as the torque transmitting element; U.C. Davis; No. 04CVT-55; pp. 1-11; 2004.
Shriner's Hospitals; Your new orthosis; http://www.shrinershq.org/patientedu/orthosis.html; pp. 1-3; (printed) Nov. 22, 2002.
Takaki et al; Load-sensitive continuously variable transmission for powerful and inexpensive robot hands; IEEE; pp. 45-46; 2004.
Takesue et al.; Development and experiments of actuator using MR fluid; IEEE; pp. 1838-1843; 2000.
Townsend Design; Functional Bracing Solutions (AIR Townsend & Ultra AIR); http://www.townsenddesign.com/air.html; 2 pgs; (printed) Nov. 21, 2002.
Townsend Design; Functional Knee Bracing Solutions; http://www.townsenddesign.com/functional.html; pp. 1; (printed) Nov. 21, 2002.
Townsend Design; Patented Motion Hinge (Planes of Motion); http://www.townsenddesign.com/motion.html; pp. 1; (printed) Nov. 21, 2002.
Trimmer et al.; An operational harmonic electrostatic motor; IEEE; pp. 13-16; 1989.
Smith et al., U.S. Appl. No. 12/471,299 entitled "Therapy and mobility assistance system," filed May 22, 2009.
Bhugra, Kern; U.S. Appl. No. 12/363,567 entitled "System and method for controlling the joint motion of a user based on a measured physiological property," filed Jan. 30, 2009.
Horst et al., U.S. Appl. No. 12/703,067 entitled "Foot pad device and method of obtaining weight data," filed Feb. 9, 2010.
Krebs et al.; A paradigm shift for rehabilitation robotics; Eng. In Medicine and Biology Magazine, IEEE; vol. 27; Issue 4; pp. 61-70; Jul. 2008.
Otto Bock Health Care; Sensor Walk White Paper; ID No. 09031595.1; pp. 1-12; 2009.

* cited by examiner

MULTI-FIT ORTHOTIC AND MOBILITY ASSISTANCE APPARATUS

PRIORITY

The present patent application claims priority to and incorporates by reference the corresponding provisional patent application Ser. No. 61/027,365, entitled, "Multi-Fit Orthotic and Mobility Assistance Apparatus" filed on Feb. 8, 2008.

FIELD OF THE INVENTION

At least certain embodiments of the invention relate generally to functional rehabilitation and mobility enhancement of patients who have suffered loss of function due to injury, disease or other condition, and more particularly, but not exclusively, to orthotic devices for functional rehabilitation.

BACKGROUND OF THE INVENTION

Devices to assist individuals with impaired mobility due to illness or injury include passive and active assistance and support devices, mobility devices and strength training devices. Passive assistance and support devices, such as canes, crutches, walkers and manual wheelchairs, provide assistance with mobility. However, individuals using such devices must supply all of the power needed by exerting forces with other muscles to compensate for the muscle that is weak or injured. Additionally, many passive assistance and support devices provide limited mobility.

Many types of existing passive knee braces are available for stabilizing the knee to prevent or recover from injury, or to provide stability for chronic conditions. Existing braces typically come in either a few standard sizes or are custom-fitted to each patient. The standard sizes often cannot conform closely to the unique shape of an individual leg and may suffer from poor fit. The custom-fitted braces are expensive and cannot be re-used by other patients after the brace is no longer needed. Both types of brace typically rely on the tightness of fit to keep them from sliding down the leg. Keeping these braces in the proper position is a largely unmet problem.

Existing orthotic designs have many points of structural contact with the subject's body. Each contact point must be custom molded to a specific shape to meet the wide array of dimensions and geometries of subjects. Otherwise, the points of contact will be sub-optimal and will result in discomfort and pain. Additionally, existing knee braces have not been designed to couple with actuators to provide active assistance. Most passive braces do not have the required structure or attachment points to allow an actuator to be coupled.

Moreover, existing devices such as continuous passive motion (CPM) machines and robotic therapy devices involve the use of an external force to flex and extend a subject's limb to induce motion. Continuous passive motion of a joint following injury, illness or surgery has been found to reduce the post-operative pain, decrease adhesions, decrease muscle atrophy, and enhance the speed of recovery, while minimizing various risks of mobilization. CPM machines slowly and gently move a subject's leg through a reciprocal cycle between a flexion position in which an angle between the subject's femur and tibia is at a minimum, and an extension in position in which the angle between the subject's femur and the tibia is at a maximum. However, CPM machines are not sufficiently small and light as to allow attachment directly to a subject's leg (or other body part) and do not allow for mobility, typically requiring the subject to be in the reclined or sitting position during operation.

SUMMARY OF THE DESCRIPTION

At least certain embodiments of the invention disclose methods and apparatuses including a multi-fit orthotic structure with an attachment system for coupling the orthotic structure to a wide variety of subjects without requiring a custom fit. In one embodiment, active mobility assistance is provided via an orthotic system capable of integrating a linear actuator and linkage system to deliver torque to the lower leg of a subject to facilitate flexion and/or extension motion of the subject's leg. The orthotic structure is attached to the subject using a textile suspension system which does not require the orthotic structure to interface directly in the knee region or at the lateral areas of the thigh and calf of the subject, thus providing an ideal fit for the widest possible range of subjects with the minimum number of required sizes. The multi-fit orthotic structure also allows a single device to be worn on either the right or left leg. Additionally, a textile suspension system may be integrated into the attachment system to dynamically adapt to a wide range of subject's geometries.

BRIEF DESCRIPTION OF THE DRAWINGS

A better understanding of at least certain embodiments of the invention can be obtained from the following detailed description in conjunction with the following drawings, in which.

DETAILED DESCRIPTION

Throughout the description, for the purposes of explanation, numerous specific details are set forth in order to provide a thorough understanding of the present invention. It will be apparent to one skilled in the art, however, that the present invention may be practiced without some of these specific details. In other instances, well-known structures and devices are shown in block diagram form to avoid obscuring the underlying principles of embodiments of the invention.

Embodiments described herein include a relatively inexpensive orthotic system for functional rehabilitation of patients who have suffered loss of function due to illness or injury. The orthotic system is designed to conform closely to the unique shape of an individual subject's leg without requiring the expense of a custom fit, while being provided in the fewest possible sizes that accommodate the widest range of subjects. Additionally, the orthotic system described herein limits the points of structural contact of the primary orthotic structure to at most two (2) contacts: one on the proximal thigh and the other on the distal shin. This arrangement accommodates the shapes and sizes of a wide variety subject's appendages which occur between the two (2) contact points. By using a suspension textile with the ability to support, pad, and lock onto the subject, the structure is provided with the points of leverage and support required to constrain movement and assist as an exoskeleton. Embodiments are capable of attachment directly to the leg to provide not only support, but active mobility assistance in addition to continuous passive motion and robotic therapy. Embodiments also accommodate a center-mounted linear actuator and bell crank linkage coupled to the lower leg orthotic structure. Center mounting of the actuator along with the adjustability of the orthotic system allow the same device to fit either the right or left leg. A unified design eliminates the costs associated with the development, manufacturing and inventory, of different devices for each leg.

Figure 1:
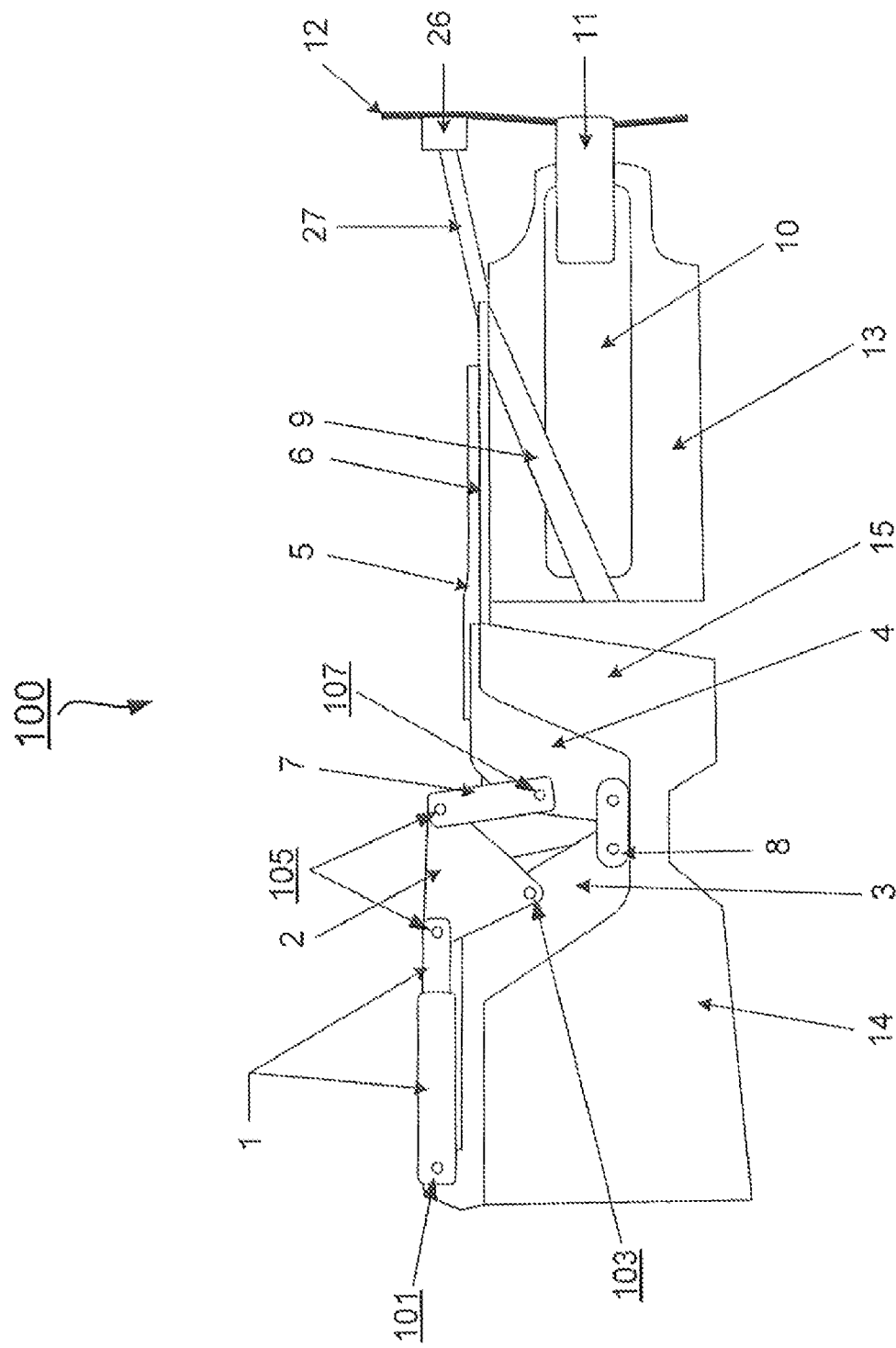
FIG. 1 is a side-viewed diagram of an orthotic system according to an exemplary embodiment of the invention.

FIG. 1 illustrates a side-view diagram of an orthotic system according to an exemplary embodiment of the invention. In the illustrated embodiment, orthotic system 100 includes: linear actuator 1; bell crank 2; thigh orthotic structure 3; lower leg orthotic structure 4; tibia anterior structure 5; tibia posterior structure 6; connector link 7; hinge 8; tibia suspension system 9; lateral support structures 10; ankle suspension structure 11; footpad sensor system 12; lower leg textiles 13; thigh textile 14; upper shin textile 15; toe strap 26; and anti-foot drop system 27. However, this is given by way of example and not limitation, as the orthotic system described herein may include fewer or more components. Linear actuator 1 acts directly on a linkage point of a bell crank rocker arm 2. The linear actuator 1 is mounted on a pivot 101 at the upper most end of the thigh orthotic structure 3; however, other embodiments would include the linear actuator 1 being constrained on a fixed plane or fixed via pivot on any portion of the thigh orthotic structure 3 or lower leg orthotic structure 4 or other structural parts. Alternate embodiments would also include indirect actuation via an input link between the linear actuator 1 and the bell crank 2.

The bell crank 2 has one or more fixed pivots 103 on the same structure as the linear actuator 1 is mounted. In one embodiment, the bell crank 2 has dual fixed pivots 103, both in a coaxial configuration with respect to one another on opposite lateral sides of the orthotic system 100. The linear actuator 1 operates on a point at or near the midline of both the orthotic system 100 and the bell crank 2 to split the forces into two (2) nearly equal components to balance torque transferred to the lower structure. The bell crank 2 has two (2) output pivots 105 in the same lateral plane as the bell crank pivots 103; however, an alternate embodiment could have fewer or more output pivots 105 which are not necessarily aligned with the bell crank pivots 103. At least certain embodiments utilize two (2) link structures 7 which transfer forces to and from the lower orthotic structure 4. The thigh orthotic structure 3 is connected to the lower leg orthotic structure 4 using one or more hinge joints 8. In one embodiment, the hinge joints 8 are located on each lateral side of the orthotic system 100 such that they can be placed in a coaxial configuration relative to the joint of the subject wearing the orthotic system 100. The orthotic system 100 uses a geared polycentric hinge joint 8; however, alternate embodiments may include the use of single pivot joints as well as other linkage systems (such as a crossed four-bar linkage or other similar multi-axis joints). The link structures 7 act on individual pivots 107 on the lower leg structure 4; however, other embodiments include fewer or more pivots 107 or spherical joints.

In the illustrated embodiment, the distal portion of the tibia posterior structure 6 is affixed to the tibia suspension system 9 such that high levels of force may be transmitted to the top of the lateral support structures 10 positioned on each of the lateral sides of the lower leg of the subject. The lateral support structures 10 transmit forces vertically to the ankle suspension structure 11 and ultimately to the ground via the foot pad sensor system 12. The lateral support structures are attached to the lower leg textiles 13 which hold each of the lower leg components relative to one another and provide wide area support to the subject's body as well as padding between hard structures and the body. In one embodiment, the thigh textile 14 is attached to the thigh orthotic structure 3 at two (2) points at the proximal end of the structure as well as two (2) points laterally near each of the hinges 8. Alternate embodiments include the thigh textile 14 to be attached at one or more points at the distal end of the thigh orthotic structure 3 as well as one or more points at the proximal end of the thigh orthotic structure 3. In one embodiment, the upper shin textile 15 is affixed to the lower leg orthotic structure 4 at two (2) lateral points near each hinge. Other embodiments include affixing the upper shin textile 15 in fewer or more places.

The tibia suspension system 9 is embodied as an adjustable webbing strap which connects the distal end of the tibia posterior structure 6 and the proximal end of the lateral support structures 10. Alternate embodiments may include a combination of vertical force carrying tension structures which transfer force from any point on the tibia length system or similar anterior structure to any point on lateral structures similar to the lateral support structures 10. The foot pad sensor system 12 may be embodied by four (4) pressure sensitive sensors encased in textile. In at least certain embodiments, two sensors are located in the forefoot area and two are located under the heel of the subject. The design is such that the foot pad sensor can be reversed to accommodate both left and right feet. An optional toe strap 26 is similarly reversible left to right and allows the footpad to be secured to the foot to eliminate a tripping hazard as well as giving a point of attachment for anti-foot drop system 27.

The illustrated embodiment includes a passive foot drop tension system 27 which may be embodied as elastic webbing connecting the forefoot loop with the lower portion of the tibia posterior structure 6. Alternate embodiments may include active foot drop devices including linear and rotational actuators placed inline between the toe strap 26 and the distal portion of the tibia posterior structure 6 or which could be hydraulic, pneumatic, electric, or remotely actuated via cable. Alternate embodiments of the foot pad sensor system 12 include any number of sensors placed throughout the footpad. Additional embodiments of the pressure sensors in the orthotic design include placement of pressure sensors in anterior and posterior portions of the textiles as well as directly on the posterior side of the orthotic system facing the subject to facilitate determining the level of pressure and forces of exerted in and around these interfaces, and to automatically instruct or warn the subject of potential problems as well as facilitate using, for example, the pressure and force information as predictive feedback to software of the linear actuator for gait analysis.

Figure 2:
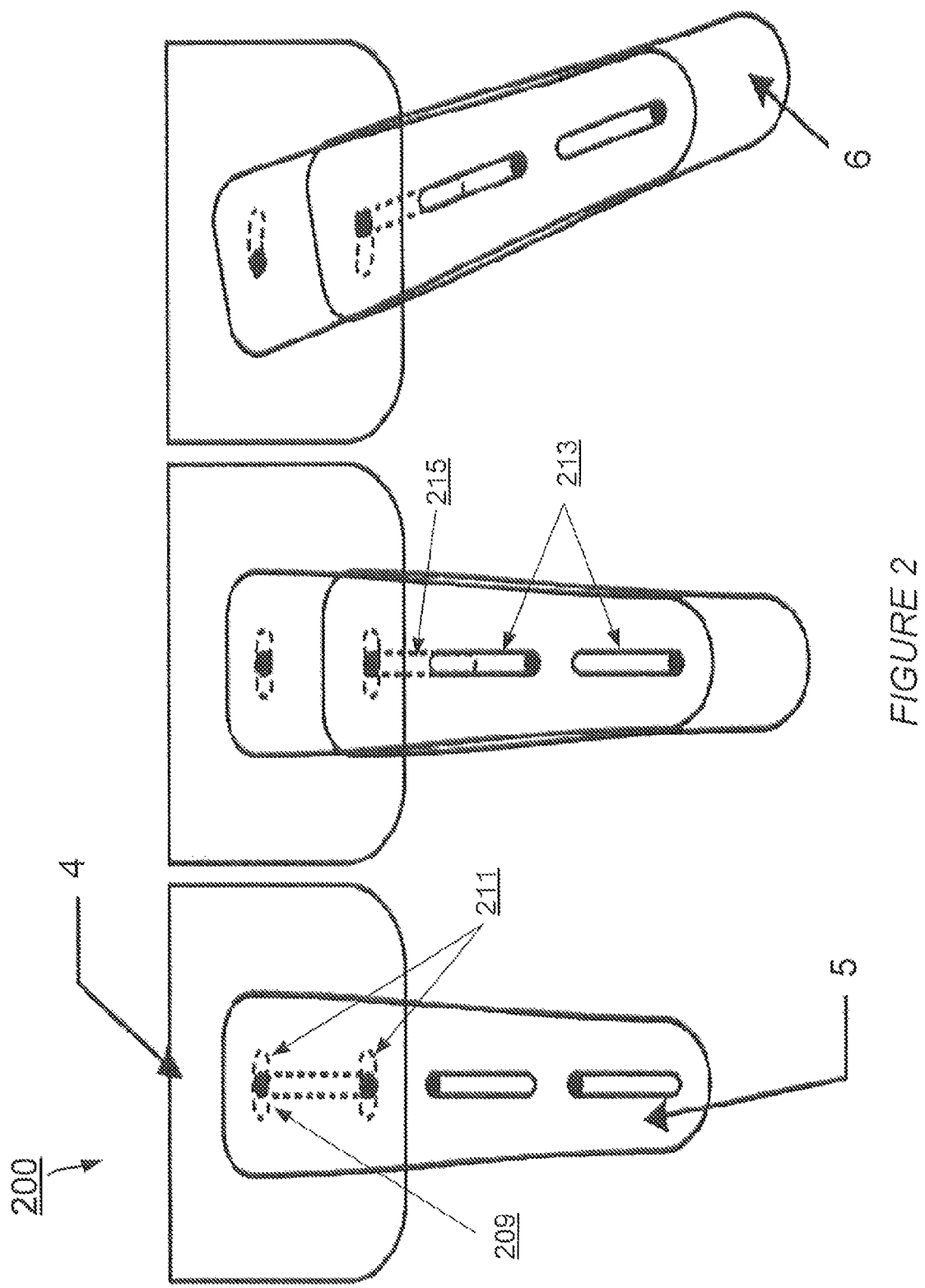
FIG. 2 shows a configuration of the tibia alignment and length adjustment system according to an exemplary embodiment of the invention.
Figure 3:
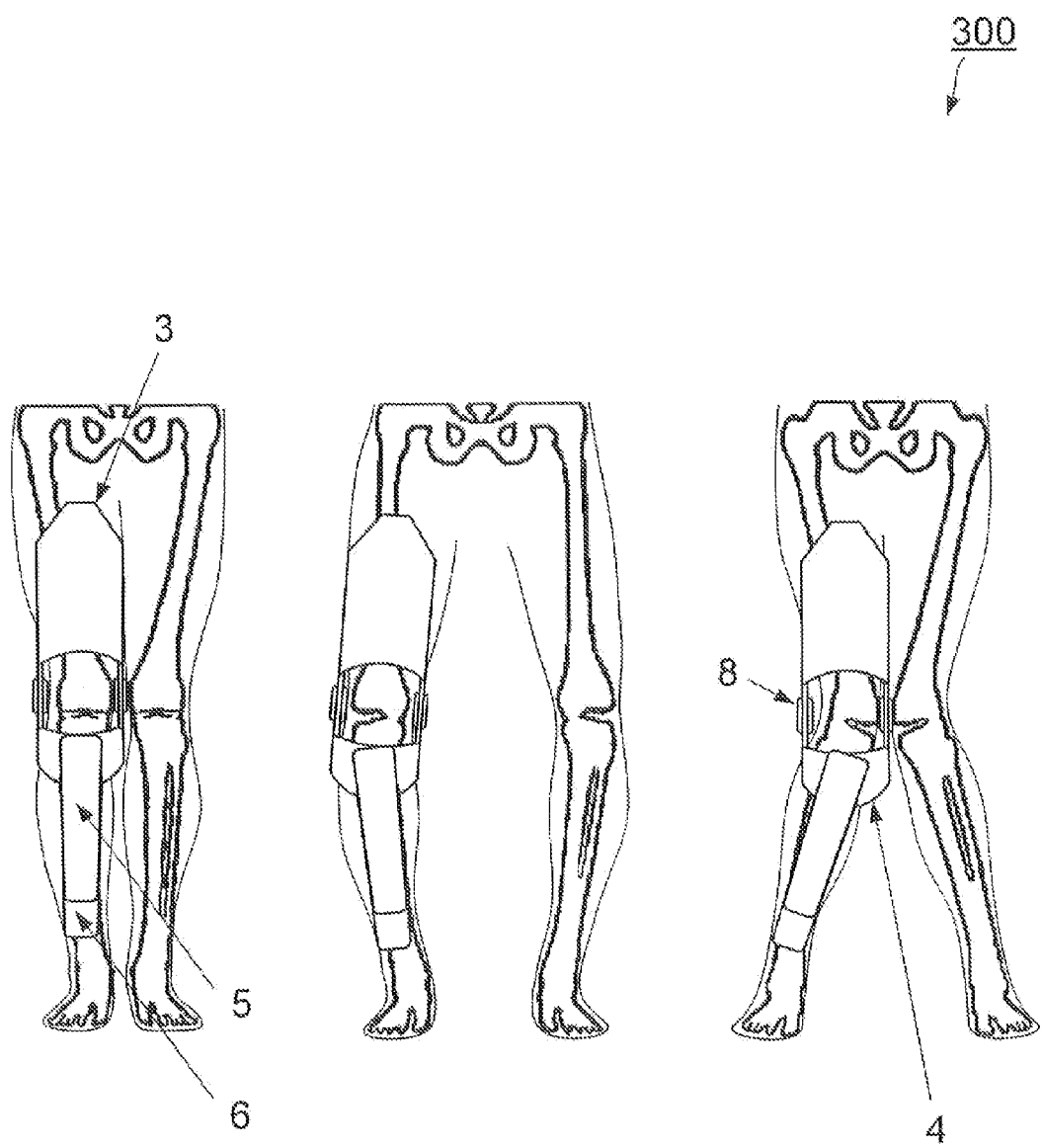
FIG. 3 illustrates examples of an orthotic system superimposed on subjects with varying degrees of leg alignment.

FIG. 2 shows a configuration of the tibia alignment and length adjustment system according to an exemplary embodiment of the invention. The tibia alignment and length adjustment system is integrated into the lower leg orthotic structure 4, the tibia anterior structure 5 and the tibia posterior structure 6. The tibia anterior structure 5 can be rotated about a point 209 on the midline of the device's lower leg orthotic structure 4. A structure with two (2) slots 211 which have constant radii about the center point allow two (2) bolts to pass through and allow the lower leg orthotic structure 4 to be coupled with the tibia anterior structure 5. This system allows the structures 4 and 5 attached to the tibia anterior structure 6 to rotate relative the thigh orthotic structure 3 and the lower leg orthotic structure 4. Alternate embodiments include a single radius slot rotating about a fixed point, multi-position bolt or circular structures. The tibia length system includes three (3) slots oriented along the proximal/distal axis, two (2) slots 213 in the distal portion of the tibia anterior structure 5 and one (1) slot 215 in the proximal end of the tibia posterior structure 6. When bolts through these slots are loosened, the tibia posterior structure 6 is allowed to move distally or proximally to adjust the length of the tibia posterior structure 6 relative to the proximal structures. Orthotic system 100 allows the tibia structures 5 attached to the tibia anterior structure 6 to rotate relative the thigh orthotic structure 3 and the lower leg orthotic structure 4 to accommodate subjects with non-linear leg structure alignment such as those depicted in FIG. 3, which illustrates examples of an orthotic system superimposed on subjects with varying degrees of leg alignment including nominal leg alignment as well as an extreme bow-legged subject and a knock-kneed subject.

Figure 4:
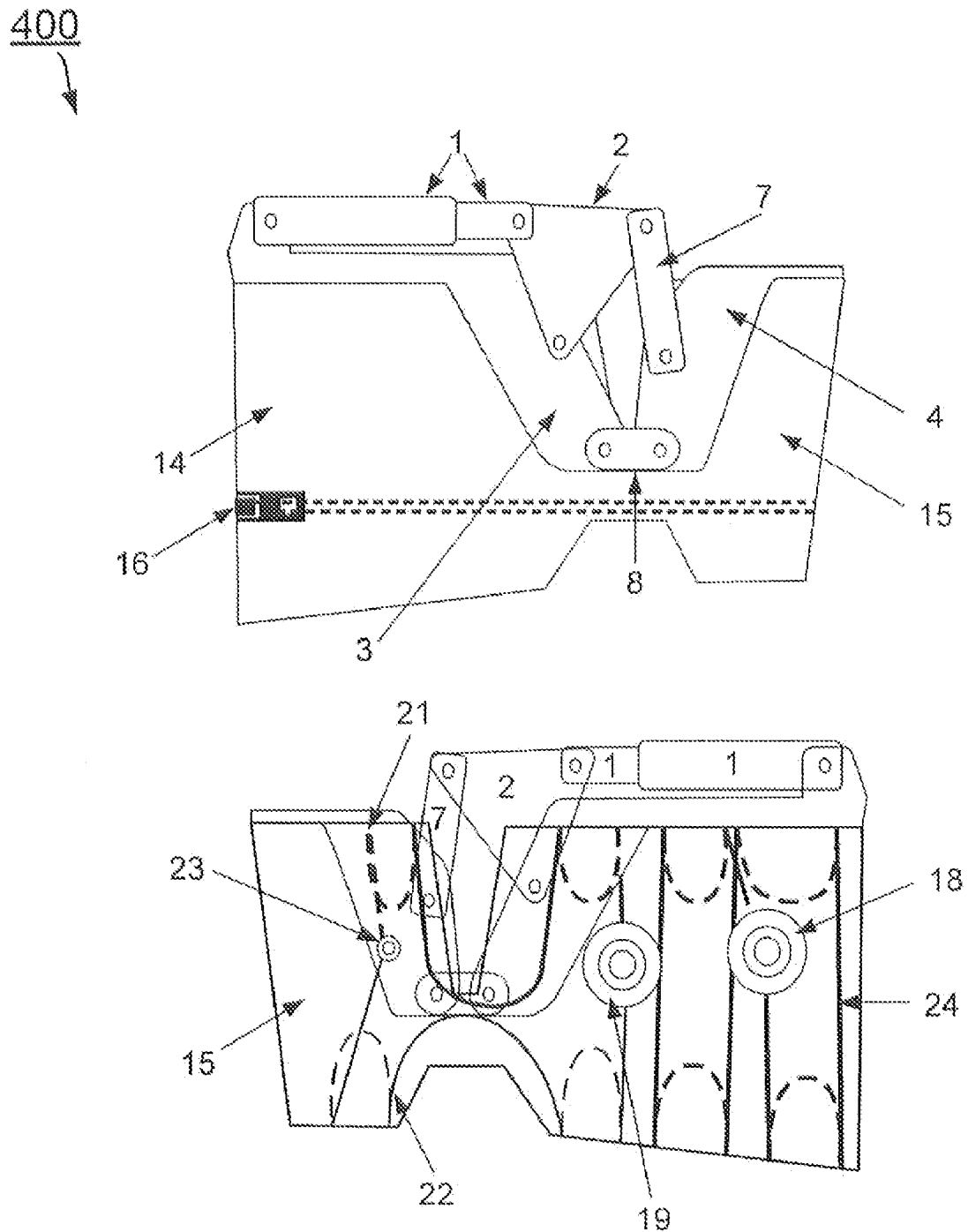
FIG. 4 illustrates a configuration of a thigh and knee textile tensioning system according to an exemplary embodiment of the invention.

FIG. 4 illustrates a configuration of a thigh and knee textile tensioning system according to an exemplary embodiment of the invention. One embodiment utilizes zipper closure 16 for the upper textile portions of the system; however, alternate embodiments could implement hook and loop, button, snap, or other similar fasteners to close and tighten the textile system. Independent cable reel tensioning systems 18 and 19 are implemented in the thigh textile system 14 to adjust tension across a broad surface area of the skin and soundly secure the orthotic system 100 to the subject. The cable reel tensioning system implements two (2) independent cable reels into the thigh textile system 14; however, alternate embodiments of the design can implement fewer or more cable reels (or fabric/webbing roller furling systems) to take up slack in the thigh textile 14 to affect textile tension and the fit of the orthotic to the subject. Additional embodiments of the tensioning system may include integration of pneumatic cells into the textile which can be statically inflated to a particular level to adjust fit to the subject or can be inflated dynamically through an inflation system (or via orthotic motion to dynamically massage the subject's appendage to assist in blood circulation through the appendage).

The illustrated embodiment of FIG. 4 includes a knee-lock tensioning system comprised of a cable reel system with loops of cable 21/22 exiting and entering the independent cable reel 19. The cable loop is routed such that one direction of the cable loop is routed along the anterior portion of both the proximal and distal sections of the subject's knee creating the anterior knee lock cable loop 21. The other direction of the same cable is routed along the posterior of the proximal and distal portions of the subject's knee while avoiding the area directly behind the knee to create the posterior knee lock cable loop 22. The cable is isolated by an isolating nut 23 such that the lengths of the anterior and posterior loops 21/22 of the knee lock system are maintained without affecting one another. The isolation nut 23 can be loosened to adjust the relative amount of cable in each of the posterior and anterior loops of cable. Alternate embodiments could implement webbing furling or webbing ratcheting systems to affect the same locking phenomenon. The knee lock system when adjusted properly locates the subject's knee joint axis in a coaxial configuration with the hinge joints 8 of the orthotic system 100.

The illustrated embodiment of FIG. 4 also includes a proximal thigh tensioning system. The independent proximal thigh cable reel 18 may be designed to induce tension and a solid, stable interface between the subject's proximal thigh and the thigh orthotic structure at the proximal end of the structure, off of which leverage may be gained when applying torque to the subject's leg. The proximal thigh tension cable 24 forms two (2) loops which cover a broad area and distribute force evenly throughout the textile. The orthotic structure has clearance near the knee and does not require structural elements in close proximity to the kneecap. This design prevents the orthotic from applying unwanted forces to the knee. The clearance allows for post-surgical bandages and allows icepacks to be applied and removed while the orthotic remains in place.

Figure 5:
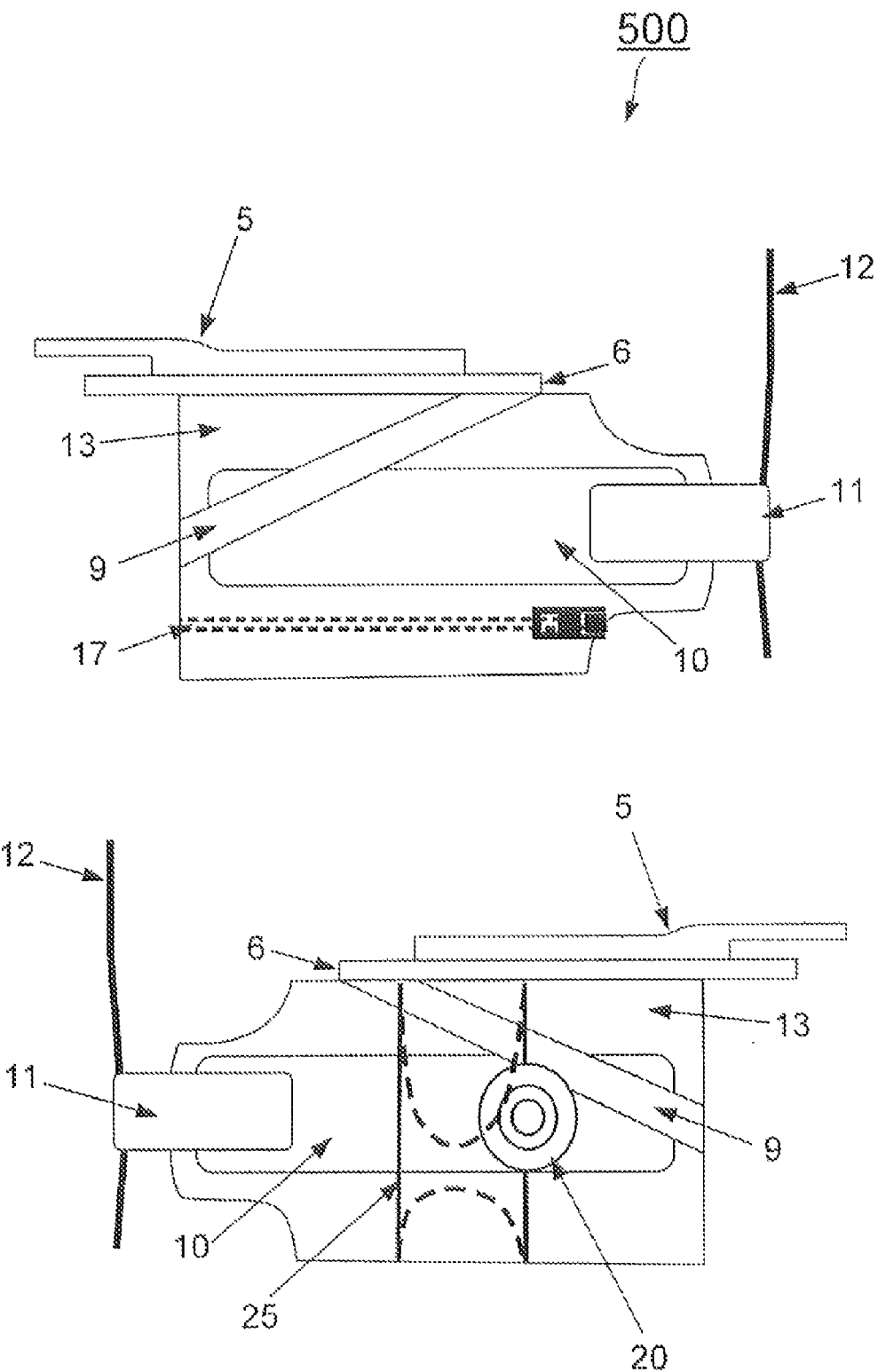
FIG. 5 illustrates a configuration of a lower shin textile tensioning system according to an exemplary embodiment of the invention.

FIG. 5 illustrates a configuration of a lower shin textile tensioning system according to an exemplary embodiment of the invention. The illustrated embodiment utilizes zipper closure 17 for the lower textile portions of the system; however, alternate embodiments could implement hook and loop, button, snap, or other similar fasteners to close and tighten the textile system. Independent cable reel tensioning system 20 is implemented in the lower leg textile system 13 to adjust the level of tension across a broad surface area of the subject's lower leg and soundly secure the orthotic system 100 to the subject. The cable is routed in a single lower shin tensioning loop 25 originating and terminating at the reel 20 and routed around the leg such that it can affect the slack between the lateral support structures 10 and the tibia posterior structure 6 as well as the portion of textile around the posterior of the subject's calf. Alternate embodiments of the design could implement a similar cable, textile, or webbing ratcheting furling or reel system.

Figure 6:
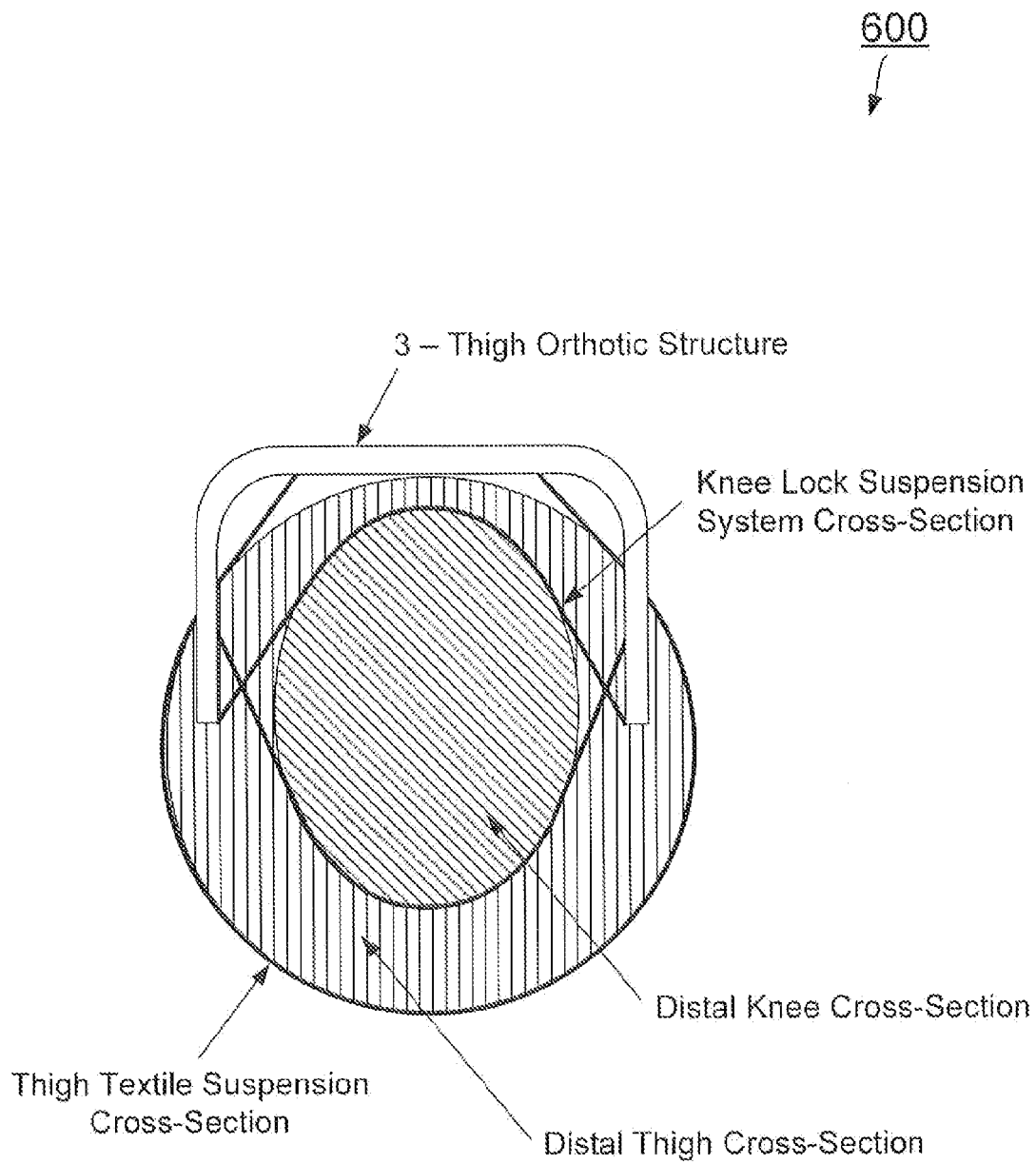
FIG. 6 illustrates a cross-sectional view of a thigh suspension mechanism according to an exemplary embodiment of the invention.

FIG. 6 illustrates a cross-sectional view of the thigh textile suspension mechanism according to an exemplary embodiment. In the illustrated embodiment, the thigh textile suspension (and similar tibia suspension system 9) keeps the thigh orthotic structure from coming into direct contact with the subject's thigh. The force may be communicated through the thigh textiles. This arrangement is of particular advantage for active orthotic systems in which force is applied by an actuator to aide in leg extension for sit-to-stand mobility and ascending stairs, and to apply force to resist gravity to aide in stand-to-sit mobility and descending stairs. The textile-based suspension is more advantageous than the padding of traditional braces because active orthotics require movement of the brace to be communicated directly into movement of the leg. If there is too much padding, movement of the brace may only compress the padding and not effectively communicate the force to the subject's leg. Use of a non-stretch fabric for the textile allows force to be communicated to a large area of the subject's leg comfortably, yet the fabric itself does not stretch allowing brace movement and leg movement to be closely coupled.

Embodiments are not limited to the techniques and materials discussed herein. The structural elements could be constructed of carbon fiber, fiberglass, aluminum, steel or another rigid material. The textile portion could be comprised of any compliant material including fabric, webbing or flexible plastics. An embodiment has been described for the knee, but braces with the same the multi-fit and mobility-assistance features could be applied to other joints such as the ankle, elbow, hip and shoulder.

Throughout the foregoing specification, references to "one embodiment," "an embodiment," "an example embodiment," indicate that the embodiment described may include a particular feature, structure, or characteristic; however every embodiment may not necessarily include the particular feature, structure, or characteristic. Moreover, such phrases are not necessarily referring to the same embodiment. When a particular feature, structure, or characteristic is described in connection with an embodiment, it is submitted that it is within the knowledge of one skilled in the art to bring about such a feature, structure, or characteristic in connection with other embodiments, whether or not explicitly described. Various changes may be made in the structure and embodiments shown herein without departing from the principles of this description.

In the description as set forth above and claims, the terms "coupled" and "connected," along with their derivatives, may be used. It should be understood that these terms are not intended to be synonymous with each other. Rather, in particular embodiments, "connected" is used to indicate that two (2) or more elements are in direct physical or electrical contact with each other. "Coupled" may mean that two (2) or more elements are in direct physical or electrical contact. However, "coupled" may also mean that two (2) or more elements are not in direct contact with each other, but yet still cooperate or interact with each other.

Embodiments of the invention may include various operations as set forth above or fewer operations or more operations, or operations in an order which is different from the order described herein. Throughout the foregoing description, for the purposes of explanation, numerous specific details were set forth in order to provide a thorough understanding of the invention. It will be apparent, however, to one skilled in the art that the invention may be practiced without some of these specific details. Accordingly, the scope and spirit of the invention should be judged in terms of the claims which follow as well as the legal equivalents thereof.

What is claimed is:

1. A multi-fit orthotic apparatus using a textile-based suspension, the apparatus comprising:
    a thigh orthotic structure coupled with a thigh suspension textile;
    a lower leg orthotic structure coupled with an upper shin suspension textile;
    a lateral support structure coupled with a lower leg suspension textile, the lateral support structure positioned on both lateral sides of a lower leg of a subject, wherein each suspension textile conforms closely to the subject to accommodate a wide range of subjects without a custom fit;
    a tibia anterior structure;
    a tibia posterior structure coupled with the tibia anterior structure; and
    a tibia suspension system coupled with the tibia posterior structure and the lateral support structure to transmit force to the lateral support structure.

2. The multi-fit orthotic apparatus of claim 1, further comprising a plurality of independent tensioning systems including:
    an independent proximal thigh textile tensioning system coupled with the thigh suspension textile, the proximal thigh textile tensioning system configured to adjust tension across a thigh of the subject and to distribute force evenly throughout the thigh suspension textile to gain leverage when applying torque to a leg of the subject;
    an independent knee-lock textile tensioning system coupled with the upper shin suspension textile, the knee-lock textile tensioning system configured to adjust tension around a knee region of the subject; and
    an independent lower shin textile tensioning system coupled with the lower leg suspension textile, the lower shin textile tensioning system configured to adjust tension across the lateral support structure.

3. The multi-fit orthotic apparatus of claim 2, wherein the independent knee-lock textile tensioning system is further configured to properly locate the subject's knee joint axis in a coaxial configuration with the hinge joints of the orthotic apparatus.

* * * * *